(12) United States Patent
Mordehai et al.

(10) Patent No.: US 6,624,409 B1
(45) Date of Patent: Sep. 23, 2003

(54) MATRIX ASSISTED LASER DESORPTION SUBSTRATES FOR BIOLOGICAL AND REACTIVE SAMPLES

(75) Inventors: Alex Mordehai, Santa Clara, CA (US); Jian Bai, Mountain View, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/208,441

(22) Filed: Jul. 30, 2002

(51) Int. Cl.$^7$ .................................. H01J 49/10
(52) U.S. Cl. ....................................... 250/288
(58) Field of Search ........................ 428/119; 250/281, 250/288, 287, 282

(56) References Cited

U.S. PATENT DOCUMENTS

| | | | |
|---|---|---|---|
| 5,118,937 A | 6/1992 | Hillenkamp et al. | |
| 5,498,545 A | 3/1996 | Vestal | |
| 5,589,684 A | * 12/1996 | Ventrudo et al. | 250/225 |
| 5,663,561 A | * 9/1997 | Franzen et al. | 250/288 |
| 5,716,825 A | 2/1998 | Hancock et al. | |
| 5,770,272 A | * 6/1998 | Biemann et al. | 427/421 |
| 5,777,324 A | 7/1998 | Hillenkamp | |
| 5,854,486 A | * 12/1998 | Dreyfus | 250/288 |
| 5,894,063 A | 4/1999 | Hutchens et al. | |
| 5,965,884 A | 10/1999 | Laiko et al. | |
| 5,994,694 A | * 11/1999 | Frank et al. | 250/281 |
| 6,004,770 A | 12/1999 | Nelson | |
| 6,040,575 A | 3/2000 | Whitehouse et al. | |
| 6,093,541 A | 7/2000 | Nelson | |
| 6,111,251 A | 8/2000 | Hillenkamp | |
| 6,175,112 B1 | 1/2001 | Karger et al. | |
| 6,245,227 B1 | 6/2001 | Moon et al. | |
| 6,265,715 B1 | 7/2001 | Perreault et al. | |
| 6,277,573 B1 | 8/2001 | Koster | |
| 6,281,493 B1 | 8/2001 | Vestal et al. | |
| 6,288,390 B1 | 9/2001 | Siuzdak et al. | |
| 6,294,790 B1 | 9/2001 | Weinberger | |
| 6,316,266 B1 | 11/2001 | Nelson | |
| 6,322,970 B1 | 11/2001 | Little et al. | |
| 6,339,177 B1 | * 1/2002 | Bergman | 568/711 |
| 6,558,744 B2 | * 5/2003 | Jarrell et al. | 427/385.5 |
| 2002/0187312 A1 | * 12/2002 | Fonash et al. | 428/195 |
| 2003/0040173 A1 | * 2/2003 | Fonash et al. | 438/622 |

* cited by examiner

*Primary Examiner*—Jack Berman
*Assistant Examiner*—Johnnie L Smith, II

(57) ABSTRACT

A substrate for matrix assisted laser desorption ionization mass spectrometry. The substrate has a layer of a nitride composition on the surface of the substrate. The nitride composition is a major amount by weight from the group of titanium nitride, zirconium nitride and hafnium nitride.

39 Claims, 2 Drawing Sheets

MATRIX ASSISTED LASER DESORPTION SUBSTRATES FOR BIOLOGICAL AND REACTIVE SAMPLES

CROSS-REFERENCE TO RELATED APPLICATIONS NOT APPLICABLE

STATEMENT REGARDING FEDERALLY SPONSORED RESEARCH OR DEVELOPMENT

This invention has been created without the sponsorship or funding of any federally sponsored research or development program.

FIELD OF THE INVENTION

This invention relates generally to the field of mass spectrometry and more particularly toward sample substrates having a surface for reduced interaction with reactive samples and laser radiation.

BACKGROUND OF THE INVENTION

There are several surface ionization techniques that are useful in mass spectrometry (hereinafter referred to as MS). Types of surface ionization include, but are not limited to, fast ion or atom bombardment, field desorption, laser desorption, plasma desorption. This technique is described more fully in U.S. Pat. No. 5,118,937 of Hillenkamp et al. and U.S. Pat. No. 5,777,324 to Hillenkamp. One of the most widely used surface ionization techniques utilizes matrix assisted laser desorption ionization (hereinafter referred to as MALDI). One of the problems of the MALDI technique is the cleanliness of the sample as well as its interaction with a substrate, which can have an influence on the sample crystallization process. For example, presence of sodium at the surface of the substrate can easily contaminate the sample to produce distorted spectra. Interpretation of this distorted data is somewhat more difficult. Also higher ionic contents on the surface of the substrate can negatively affect the sensitivity of the technique by decreasing the ion yield for the sample. Also surface reactivity is a concern with reactive samples. Ideally, the sample should stay intact during the analysis. For example, gold plated substrates commonly produce satisfactory results. Also there were several attempts to use stainless steel and amorphous silicon as sample substrates.

A variation of the MALDI technique involves the elimination of the matrix and the introduction of a sample substrate surface which reacts with the sample. An example of this modified MALDI technique is illustrated in U.S. patent of Siuzdak et al. U.S. Pat. No. 6,288,390. This patent describes a porous light-absorbing semiconductor substrate. The patent describes an extensive list of light absorbing materials. When the source of radiation irradiates the substrate under reduced pressure and an analyte from the sample is absorbed on the substrate, the irradiation also causes the desorption and ionization of the analyte. Although this technique eliminates the need for a matrix, the substrate must be replaced after limited use.

These and other difficulties associated with laser desorption/ionization techniques for mass spectrometry, with and without the use of matrix, have been obviated by the present invention.

It is, therefore, a feature of the present invention to provide an apparatus for spectroscopic analysis which utilizes the MALDI technique and which includes a sample substrate that is chemically inert to the material in the sample to be analyzed and to the materials in the matrix with respect to sample degradation and contamination at the substrate.

Another feature of the invention is to provide a sample substrate for an analyzer using MALDI that is relatively electrically conductive and non light absorbing.

A further feature of the invention is to provide a sample substrate for an analyzer using MALDI that has mechanical hardness and resists sample penetration into the substrate surface during application of the sample to the surface and irradiation by the laser.

Still another feature of the invention is the provision of a sample substrate that is easy to clean and which can be reused for many sample cycles.

Another feature of the invention is the provision of a sample substrate that is inexpensive and that can be treated as disposable, offering, for example, an inexpensive way for archiving a portion of the sample by archiving it with the substrate.

SUMMARY OF THE INVENTION

The present invention relates to an apparatus and method for use with a mass spectrometer (MS) or MS system with MALDI. The substrates of the present invention have a surface for reduced interaction with sample and comprises a surface having an inorganic, conductive nitride compound which is at least a major amount by weight from the group of titanium nitride, zirconium nitride and hafnium nitride. The nitride compound may be, for example, a mixed metal nitride such as an aluminum titanium nitride or chromium-titanium-nitride. Titanium-carbon-nitride may also be used.

The invention also provides a method of producing a substrate surface having reduced interaction of a reactive sample. The method comprises applying a coating to a substrate body selected from the group consisting of titanium nitride, zirconium nitride and hafnium nitride of metals to the surface of the substrate.

The invention also relates to a MALDI apparatus for providing an ionized sample of material to an analysis instrument that includes the improved substrate of the present invention. The invention further relates to a mass spectrometer that includes the substrate of the present invention with MALDI apparatus for providing an ionized sample of material to the mass spectrometer.

BRIEF DESCRIPTION OF THE DRAWINGS

The invention is described in detail below with reference to the following figure.

DETAILED DESCRIPTION OF THE INVENTION

Figure 1:
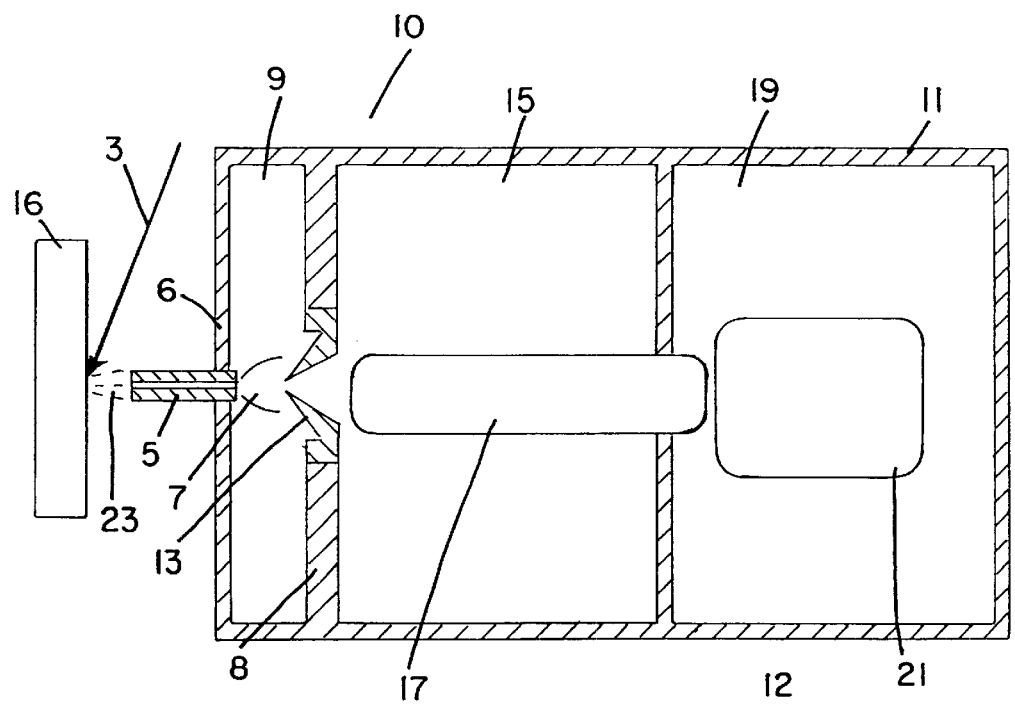
FIG. 1 is a diagrammatic view of the present invention and its application to a mass spectrometer.

FIG. 1 shows an application of the present invention. Although the figure illustrates an AP (atmospheric pressure) MALDI technique, the invention should not be construed narrowly to include only this particular type of MALDI and system and can be applied also to vacuum MALDI and fast atom bombardment (FAB) known in the art.

Referring now to FIG. 1, an example of a mass spectrometer with the present invention is generally indicated by the reference numeral 10 includes a housing 11 and a sample substrate 16. Housing 11 includes a first vacuum chamber 9 between a front wall 6 and a first inside wall 8, a second vacuum chamber 15 between wall 8 and second inside wall 12 and a third vacuum chamber 19. Although three vacuum chambers are shown in the diagram, any number of chambers may be used with the present invention. An ionized sample 23 is produced by laser radiation applied from the direction indicated by arrow 3 onto a sample and matrix deposited on the substrate 16. Ions produced at atmospheric pressure are collected by a sampling capillary 5. Sampling capillary 5 is positioned in the front wall 6 and connects the atmospheric pressure region to the first vacuum chamber 9. A skimmer 13 is located in the first inside wall 8 between first vacuum chamber 9 and second vacuum chamber 15. An ion optics system 17 is located in chamber 15 and extends from the skimmer 13 to a mass analyzer 21 located in chamber 19. The sampled ion beam is transferred by ion optics system 17 towards the mass analyzer 21. Other combinations, systems and embodiments are possible with the present inventions that are well known in the art.

Figure 2:
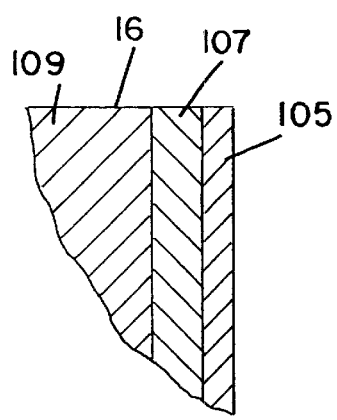
FIG. 2 is a fragmentary view of the surface area of the substrate on an enlarged scale.

Referring to FIG. 2, the substrate 16 comprises a substrate body 109, a metal layer 107 and a nitride compound layer 105. According to the present invention, the substrate body 109 can be made out of aluminum, stainless steel, glass or plastic, conductive or non-conductive solid material or film. In one embodiment, the substrate body 109 is made out of aluminum. The second layer is an intermediate metal layer that provides good adhesion for the nitride compound layer 105 to the substrate body 109. It is recognized that depending on the particular manufacturing process it may be not necessary to incorporate the second layer into the substrate design. For example, in case of a stainless steel substrate body 109, it is possible to fix the titanium nitride directly to the substrate body, resulting only in a two layer substrate. It was also found that for a substrate body portion of aluminum, it is possible to use an intermediate electroless nickel layer 107 to provide good adhesion and uniformity of the nitride coating. It was also found that a thin layer of the metal which forms the nitride compound provides good adhesion of the nitride compound to a substrate body substrate 109 made out of glass. However, it is important to the invention that the nitride surface or layer be on the exterior of substrate 16 to reduce interaction with the reactive sample or laser radiation.

Inorganic, conductive nitride compounds from the group of titanium nitride, zirconium nitride and hafnium nitride unexpectedly render the surface of substrate 16 more inert with respect to certain known reactive analytes than typical substrate surface materials such as stainless steel, gold, nickel. Those reactive analytes include, but are not limited to, proteins, peptides and nicotinic acid. The conductive nitride compound may be a titanium nitride, zirconium nitride or hafnium nitride, or a mixed metal nitride such as an titanium aluminum nitride. Titanium nitride, zirconium nitride, and hafnium nitride exhibit exceptionally inert properties with respect to many such analytes. Other nitride compounds include, but are not limited to, titanium carbon nitride, chromium titanium nitride, and tungsten titanium nitride. However, the mixed metal nitride compounds should be a major amount by weight from the group of titanium nitride, zirconium nitride and hafnium nitride and a minor amount by weight of an element other than titanium, zirconium and hafnium that is capable of forming a nitride. In addition, the nitride compounds of the present invention in general, exhibit other properties that are particularly beneficial for mass spectrometry applications. For example, the nitride compounds of the present invention, when coated on surfaces of a substrate are extremely hard and allow parts coated therewith to be cleaned using relatively hard abrasives. The nitride compounds of the present invention exhibit hardness greater than about 2000 kg/mm Knoop or Vicker Microhardness, typically about 2500 to about 3500. This translates to about 85 Rc. In addition, some nitride compounds exhibit microstructural polymorphism that may or may not depend on the stoichiometry of the compound. Polymorphism may be the result of how the compound is formed. As an aside, for some nitride films deposited on a substrate surface, e.g., titanium nitride on a metal substrate, it has been observed that the hardness of the film depends on the hardness of the substrate.

If the substrate is coated with a dielectric, static charge will accumulate on the substrate over time. Such charging may cause degradation of the ionization efficiency. Thus, if an inert coating is employed on any surface of the substrate, it can be advantageous that the coating be sufficiently electrically conductive to allow dissipation of charge. The nitrode compounds of the present invention have electrical resistivities no greater than about $10^{-1}$ ohm-cm, preferably no greater than about $10^{-3}$ ohm-cm, provide a conductive surface that is resistant to the surface absorption of the certain ionic compound, such as organic salts of sodium, more than materials with higher resistively. Irrespective of the resistivity of the coating, the coating should be uniformly deposited to insure that there are no uncoated areas or pinholes as well as to provide sufficient coverage to mask active sites on the surface.

There are many methods that can be employed to coat the compounds of the present invention onto the surface of the substrate. One method involves a two-step process: depositing a thin layer of a metal or alloy on the surface of interest and exposing the surface to an appropriate element under reaction conditions effective to form the desired compound. There are many ways in which a thin layer of metal can be deposited, e.g., by evaporation, sputtering, electroplating, chemical vapor deposition (CVD), physical vapor deposition (PVD), etc, as is known in the art. It is notable, though, that not all methods of metallic layer deposition can be employed with ease for any particular metal. For example, a metal with a low melting point or boiling point temperature is particularly suitable for deposition through evaporation. Conversely, metals with a high melting point are not easily deposited through evaporation. Once a layer of metal is deposited, the layer can be exposed to nitrogen under suitable conditions to form the desired compound. For example, metal layer surfaces may be exposed to glow discharge plasma. With nitride, a substrate having a metal layer surface is placed in a vacuum chamber. Then, ionized nitrogen gas is combined with other gases and a high voltage is applied to strike a glow to react with the substrate. It is evident that proper film formation conditions may involve high temperature processing; therefore, the material on which the surface is to be converted must be able to withstand all processing conditions. In addition, conversion of a metal layer into a compound of the present invention depends on the diffusion rate of the nitrogen into the metal layer, and such conversion may be inefficient for some compounds of the present invention. Alternatively, the compounds of the present invention may be deposited on the surface in vacuum processes that do not involve two discrete steps as described above. Such vacuum processes include, but are not limited to, cathodic arc PVD, electron-beam evaporation, enhanced arc PVD, CVD, magnetronic sputtering, molecular beam epitaxy, combinations of such techniques and a variety of other techniques known to one of ordinary skill in the art. One of ordinary skill in the art will recognize that CVD usually involves heating a substrate surface to a sufficiently high temperature to decompose gaseous organic species to form the desired film. Such heating usually precludes the use of plastic as a surface on which the film is deposited. PVD, on the other hand, does not necessarily exclude plastics as a substrate and allows for masked film deposition. However, the method coats only surfaces that are within the "line of sight" of the source of the coating material, and "blind" spots are not coated. In addition, some substrate heating may be employed in physical vapor deposition to promote film adhesion. In the case of titanium nitride, hollow cathode discharge ion plating has been widely used. This method involves depositing titanium in the presence of nitrogen gas as a reactive gas. In hollow cathode discharge ion plating, dense films can be formed as titanium molecules are evaporated while nitrogen gas is introduced. Care must be taken, however, to ensure optimal deposition. If energy in the process is too low, the evaporated titanium does not react with the nitrogen and the resultant film does not adhere well to the surface. On the other hand, excessive energy results in reevaporation from the substrate or damages to the surface.

The surface of the invention can be provided using the above methods. Generally, the coating of the invention can be deposited having a thickness from about 1000 angstroms to about 10 microns. Thickness achieved with PVD are normally about 0.5 to about 2 microns, and CVD processes normally result in thickness of about 2 to about 5 microns. It is notable that adhesion between the compound of the present invention and the surface tends to be of marginal quality at very high thickness. In addition, differences in thermal expansion coefficient between the coating layer and the surface on which the coating is deposited can also contribute to adhesion problems if the surfaces are subject to drastic changes in temperature.

The particular coating technique used generally affects the microstructure, morphology, and other physical characteristics of the deposited material. In addition, when the aforementioned deposition techniques are employed, variations in processing parameters can substantially change the morphology of the deposited film. In general, it is desirable to produce a smooth film of generally uniform thickness. Smooth films tend to provide a lower surface area, thereby rendering the film kinetically unfavorable for reaction with analytes. Smoothness of the film will, however, be highly dependent on, and in general determined by, the smoothness of the underlying surface. As another alternative, the surface coating material can be applied as a powder. One method of powder application involves providing the conductive compound in powdered form and employing high pressure to spray the powder entrained in a fluid at high velocity such that the powder mechanically adheres to the surface. Another method involves suspending the powder in a solvent to form paint, applying the paint onto the surface, and evaporating the solvent. The solvent can be a relatively inert carrier or one that facilitates chemical bonding between the powder particles or between the powder and the surface. In addition, heat can be applied to evaporate the solvent or to promote chemical bonding. Typically, no organic binder is used because organic materials generally outgas at sufficiently high vapor pressure to produce a gas phase that is ionized along with the sample, producing a high background in the mass spectrum. However, the film of the present invention does not necessarily preclude inclusion of a small amount of an organic binder if overall outgassing is sufficiently low Variations of the foregoing will be apparent to those of ordinary skill in the art. For example, while these coatings may be applied to surfaces composed of stainless steel, such coatings can also be applied to other surfaces such as plastic, glass or ceramic or other structural materials. Also it is recognized that certain surface texture (for example mat vs. polished) can be achieved with titanium-nitride upper layer by changing the surface texture for the structural material of the substrate that can provide certain advantages for the sample crystallization with respect to the subsequent ionization process.

In addition, some compounds will be especially inert with respect to some analytes, and a particular coating may be applied to a surface that is designed for exposure to a specific sample. The substrates of the present invention can be used with different surface ionization techniques including but not limiting to the fast atom bombardment. Also it is recognized that substrates can have nitride surfaces of the present invention masked with other materials such as teflon, as well known in the art, to provide multi well sample substrates. It is also recognized that substrate can be made of special shape to facilitate the sample deposition as well as sample ionization.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

EXAMPLE 1

Figure 3:
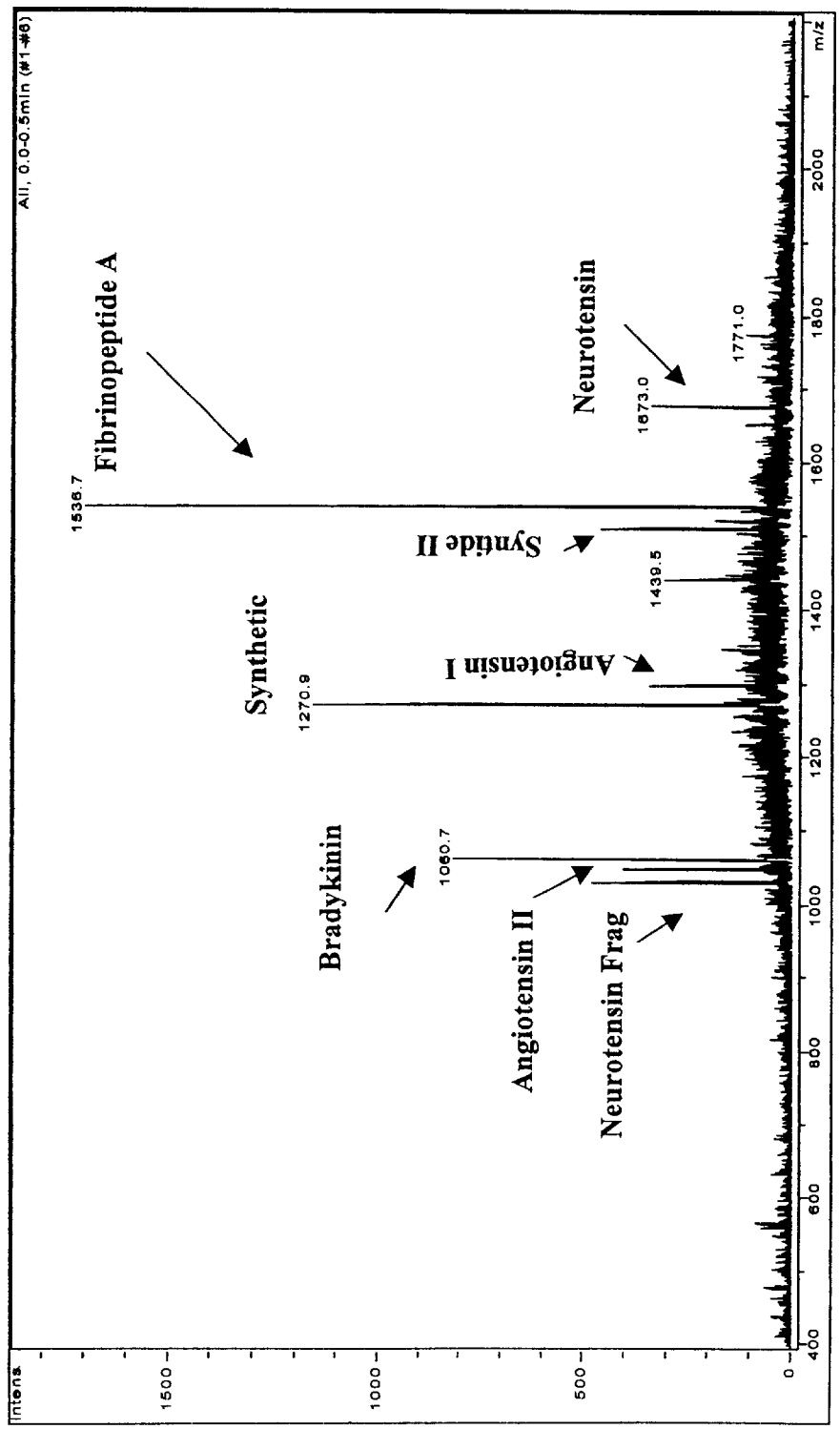
FIG. 3 shows a spectrum of 250 attomoles of each of the 8 peptides (neurotensin Frag., angiotensin II, bradykinin, synthetic peptide, angiotensin I, syntyde II, fibrinopeptide A, and neurotensiun) deposited on the titanium nitride coated substrate according to the present invention.

FIG. 3 shows a spectrum of 250 attomoles of each of the 8 peptides (neurotensin Frag., angiotensin II, bradykinin, synthetic peptide, angiotensin I, syntyde II, fibrinopeptide A, and neurotensiun) deposited on the titanium nitride coated substrate according to the present invention. Usually it is a challenge for MALDI/MS technique to obtain a spectrum with all of mixed components to be observed in the spectrum. The task identifying each of the individual components from the mixture is even more complicated at low absolute weight amount per individual component (somewhat below 5 femtomoles). In the spectrum shown in FIG. 3, all of the peptides from the mixture are observed as protonated molecular ion peaks even at much lower absolute weight amounts (i.e. at 250 attomoles) virtually with no sodium or other interfering adducts observed. The TiN substrate of the present invention provided extremely inert and favorable surface as a sample substrate for the MALDI/MS. It was possible also to wash the sample from the substrate.

What is claimed is:

1. A substrate for matrix assisted laser desorption ionization mass spectrometry comprising:
    (a) a body having a supporting surface; and
    (b) a layer of nitride composition fixed to said supporting surface, said nitride composition being a major amount by weight from the group of titanium nitride, zirconium nitride and hafnium nitride.

2. The substrate as recited in claim 1, wherein said supporting surface is stainless steel.

3. The substrate as recited in claim 1, wherein said nitride composition is titanium nitride.

4. The substrate as recited in claim 1, wherein said nitride composition is zirconium nitride.

5. The substrate as recited in claim 1, wherein said nitride composition includes a minor amount by weight of an element other than titanium, zirconium and hafnium that is capable of forming a nitride.

6. The substrate as recited in claim 5, wherein said element is aluminum.

7. The substrate as recited in claim 5, wherein said element is carbon.

8. The substrate as recited in claim 5, wherein said element is chronium.

9. The substrate as recited in claim 1, wherein said nitride composition has a surface hardness of at least 2000 kg/mm Knoop or Vicker Microhardenss.

10. The substrate as recited in claim 1, wherein said nitride composition has an electrical resistivity no greater than $10^{-1}$ ohm-cm.

11. The substrate as recited in claim 1, wherein said layer of nitride composition is fixed to said supporting surface by an intermediate layer of material.

12. The substrate as recited in claim 11, wherein said intermediate layer of material is metal.

13. The substrate as recited in claim 11, wherein said body is aluminum and said intermediate layer of material is electroless nickel.

14. The substrate as recited in claim 11, wherein said supporting surface is glass and said intermediate layer of material is titanium.

15. A method of producing a substrate for biological and reactive samples on a supporting surface in a mass spectrometer, said method comprising applying a layer of a nitride composition on said supporting surface, said nitride composition being a major amount by weight from the group of titanium nitride, zirconium nitride and hafnium nitride.

16. The method as recited in claim 15, wherein said supporting surface is stainless steel.

17. The method as recited in claim 15, wherein said nitride composition is titanium nitride.

18. A method of producing a substrate for biological and reactive samples in a mass spectrometer, said method comprising:
  (a) depositing on a supporting surface of the substrate a layer of an elemental material from the group of titanium, zirconium and hafnium; and
  (b) exposing said elemental material to nitrogen under reactive conditions to convert said layer into a nitride composition.

19. The method as recited in claim 18, wherein said depositing comprises evaporating.

20. The method as recited in claim 18, wherein said depositing comprises sputtering.

21. The method as recited in claim 18, wherein said depositing comprises electroplating.

22. The method as recited in claim 18, wherein said depositing comprises vapor deposition.

23. The method as recited in claim 18, wherein said depositing comprises physical vapor deposition.

24. The method as recited in claim 18, wherein said exposing step comprises exposing said elemental material exposing to a glow discharge plasma that includes nitrogen gas.

25. The method as recited in claim 18, wherein exposing comprises:
  (a) creating a sub-atmospheric pressure gas mixture that includes nitrogen; and
  (b) applying a voltage to said gas mixture to form a glow in said gas mixture and cause said nitrogen gas to react with said elemental material.

26. Apparatus for providing an ionized sample of material to an analysis instrument, the apparatus comprising:
  (a) a substrate for holding a specimen of material from which said sample is derived, said substrate having a body that has a supporting surface and a layer of nitride composition fixed to said supporting surface, said nitride composition being composed of a major amount by weight from the group of titanium nitride, zirconium nitride, and hafnium nitride;
  (b) light means directed at said layer for illuminating said specimen to cause desorption of material from the specimen to form ions of said material; and
  (c) an interface for capturing said ions and for delivering said ions to said analysis instrument.

27. The apparatus as recited in claim 26, wherein said nitride composition is primarily by weight titanium nitride.

28. The apparatus as recited in claim 26, wherein said nitride composition is primarily by weight zirconium nitride.

29. The apparatus as recited in claim 26, wherein said nitride composition has an electrical resistivity no greater than $10^{-1}$ ohm-cm.

30. The apparatus as recited in claim 26, wherein said nitride composition includes a minor amount by weight of an element other than titanium, zirconium, and hafnium that is capable of forming a nitride.

31. The apparatus as recited in claim 26, wherein said light means is a laser.

32. The apparatus as recited in claim 26, wherein said interface comprises:
  (a) a housing having a first vacuum chamber and a second vacuum chamber adjacent said first vacuum chamber;
  (b) a sample capillary extending from said substrate to said first vacuum chamber for conveying said ions to said first vacuum chamber;
  (c) a skimmer between said first vacuum chamber and said second vacuum chamber for directing said ions into said second vacuum chamber; and
  (d) ion optics located in said second vacuum chamber for focusing said ions to said analysis instrument.

33. A mass spectrometer comprising:
  (a) an analysis instrument for analyzing an ionized sample of material;
  (b) a substrate for holding a specimen of material from which said sample is desired, said substrate having a body that has a supporting surface and a layer of nitride composition fixed to said supporting surface, said nitride composition being composed of a major amount by weight from the group of titanium nitride, zirconium nitride, and hafnium nitride;
  (c) light means directed at said layer for illuminating said specimen to cause desorption of material from the specimen to form ions of said material; and
  (d) an interface for capturing said ions and for delivering said ions to said analysis instrument.

34. The mass spectrometer as recited in claim 33, wherein said nitride composition is primarily by weight titanium nitride.

35. The mass spectrometer as recited in claim 33, wherein said nitride composition is primarily by weight zirconium nitride.

36. The mass spectrometer as recited in claim 33, wherein said nitride composition has an electrical resistivity no greater than $10^{-1}$ ohm-cm.

37. The mass spectrometer as recited in claim 33, wherein said nitride composition includes a minor amount by weight of an element other than titanium, zirconium, and hafnium that is capable of forming a nitride.

38. The mass spectrometer as recited in claim 33, wherein said light means is a laser.

39. The mass spectrometer as recited in claim 33, wherein said interface comprises:

(a) a housing having a first vacuum chamber, a second vacuum chamber, and third vacuum chamber which contains said analysis instrument, said second vacuum chamber being located between said first vacuum chamber and said third vacuum chamber;

(b) a sample capillary extending from said substrate to said first vacuum chamber for conveying said ions to said first vacuum chamber;

(c) a skimmer between said first vacuum chamber and said second vacuum chamber; and (d) ion optics located in said second vacuum chamber, said ion optics extending from said skimmer and into said third vacuum chamber to said analysis instrument for focusing said ions to said analysis instrument.

* * * * *